US010225659B2

(12) United States Patent
Shao et al.

(10) Patent No.: US 10,225,659 B2
(45) Date of Patent: Mar. 5, 2019

(54) SPEAKER DEVICE CAPABLE OF RESTRAINING POLARIZATION, METHOD FOR ADJUSTING DIAPHRAGM BALANCE POSITION, AND METHOD FOR ADJUSTING DIAPHRAGM COMPLIANCE PERFORMANCE

(71) Applicant: Goertek.Inc, Weifang, Shandong (CN)

(72) Inventors: Minghui Shao, Weifang (CN); Jianbin Yang, Weifang (CN)

(73) Assignee: Goertek.Inc, Weifang, Shandong (CN)

( * ) Notice: Subject to any disclaimer, the term of this patent is extended or adjusted under 35 U.S.C. 154(b) by 0 days.

(21) Appl. No.: 15/551,254

(22) PCT Filed: Nov. 26, 2015

(86) PCT No.: PCT/CN2015/095681
§ 371 (c)(1),
(2) Date: Aug. 15, 2017

(87) PCT Pub. No.: WO2016/155341
PCT Pub. Date: Oct. 6, 2016

(65) Prior Publication Data
US 2018/0035211 A1 Feb. 1, 2018

(30) Foreign Application Priority Data
Mar. 31, 2015 (CN) .......................... 2015 1 0148535

(51) Int. Cl.
*H04R 9/02* (2006.01)
*H04R 7/10* (2006.01)
(Continued)

(52) U.S. Cl.
CPC ............... *H04R 9/025* (2013.01); *H04R 7/26* (2013.01); *H04R 9/06* (2013.01); *H04R 7/10* (2013.01); *H04R 29/001* (2013.01); *H04R 31/003* (2013.01)

(58) Field of Classification Search
CPC .......... H04R 9/06; H04R 9/025; H04R 19/01; H04R 19/013; H04R 19/016; H04R 2201/003; H04R 23/02
(Continued)

(56) References Cited

U.S. PATENT DOCUMENTS

2005/0276434 A1 12/2005 Kobayashi et al.
2012/0177215 A1\* 7/2012 Bose .................... G01D 5/2417
381/74
(Continued)

FOREIGN PATENT DOCUMENTS

CN 102790937 A 11/2012
CN 104185127 A 12/2014
(Continued)

OTHER PUBLICATIONS

International Search Report dated Feb. 29, 2016 in International Patent Application No. PCT/CN2015/095681.
(Continued)

*Primary Examiner* — Sunita Joshi
(74) *Attorney, Agent, or Firm* — Michele V. Frank; Venable LLP

(57) ABSTRACT

The present invention discloses a speaker device capable of restraining polarization, a method for adjusting a diaphragm balance position of the speaker device and a method for adjusting diaphragm compliance performance of the speaker device. The speaker device comprises a vibration system, a magnetic circuit system, a shell accommodating the vibration system and the magnetic circuit system, a first electret
(Continued)

layer, a second electret layer and a third electret layer, wherein the first electret layer, the second electret layer and the third electret layer have the same electric charge polarity; the first electret layer is attached to the vibration system; the second electret layer is attached to a first fixing component above the vibration system and opposite to the first electret layer; the third electret layer is attached to a second fixing component below the vibration system and opposite to the first electret layer; and the first electret layer, the second electret layer and the third electret layer are parallel to one another. In the present invention, an electrostatic field force is adopted to restrain the polarization of a diaphragm in a vibration direction.

14 Claims, 5 Drawing Sheets

(51) Int. Cl.
 *H04R 7/26* (2006.01)
 *H04R 9/06* (2006.01)
 *H04R 29/00* (2006.01)
 *H04R 31/00* (2006.01)

(58) Field of Classification Search
 USPC .................. 381/113, 116, 174, 175, 191
 See application file for complete search history.

(56) References Cited

U.S. PATENT DOCUMENTS

2014/0169593 A1 6/2014 Kwon et al.
2016/0212546 A1* 7/2016 Salvatti .................. H04R 9/06

FOREIGN PATENT DOCUMENTS

CN 104768111 A 7/2015
CN 204442673 U 7/2015

OTHER PUBLICATIONS

Written Opinion dated Feb. 29, 2016 in International Patent Application No. PCT/CN2015/095681.

* cited by examiner

SPEAKER DEVICE CAPABLE OF RESTRAINING POLARIZATION, METHOD FOR ADJUSTING DIAPHRAGM BALANCE POSITION, AND METHOD FOR ADJUSTING DIAPHRAGM COMPLIANCE PERFORMANCE

This application is a National Stage of International Application No. PCT/CN2015/095681, filed Nov. 26, 2015, which claims priority to Chinese Patent Application No. 201510148535.8, filed Mar. 31, 2015, both of which are hereby incorporated by reference in their entireties.

TECHNICAL FIELD

The present invention relates to a speaker device capable of restraining polarization, a method for adjusting a diaphragm balance position of the speaker device and a method for adjusting diaphragm compliance performance of the speaker device.

BACKGROUND

With respect to micro speaker modules, in general, module devices are asymmetrical. Meanwhile, it is difficult to avoid process tolerance in a micro speaker module assembling process, which will usually cause polarization of a diaphragm of a micro speaker in a case of large displacement. The polarization is mainly shown in a way that displacements of four corner locations of a reinforcing part are different. That is, the displacements of a diaphragm plane in a vibration direction are not uniform.

Moreover, requirements on internal magnetic gaps and external magnetic gaps are higher and higher in the market, and the increasingly reduced magnetic gaps will become more and more sensitive to the polarization of the diaphragm.

The polarization of the diaphragm will bring the following problems.

(1) Non-uniform displacements in the vibration direction will cause distributed stress of the diaphragm plane. As a result, stress of a local block is likely to become overlarge, resulting in excessive fatigue, even cracking of the diaphragm.

(2) The non-uniform displacements in the vibration direction will also cause deflection of a voice coil between in a magnetic gap, such that the voice coil will have frictional collision with a magnetic circuit.

At present, spider are adopted in micro speakers to alleviate polarization of products. Although the spider restrains polarization mainly through a mechanical restoring force, it will occupy a certain space. Meanwhile, a process for applying the spider to the micro speakers faces greater challenges.

SUMMARY

An object of the present invention is to provide a new technical solution for restraining polarization of a speaker.

According to a first aspect of the present invention, there is provided a speaker device capable of restraining polarization, the speaker device comprising: a vibration system, a magnetic circuit system, a shell accommodating the vibration system and the magnetic circuit system, a first electret layer, a second electret layer and a third electret layer, wherein the first electret layer, the second electret layer and the third electret layer have the same electric charge polarity; the first electret layer is attached to the vibration system; the second electret layer is attached to a first fixing component above the vibration system and opposite to the first electret layer; the third electret layer is attached to a second fixing component below the vibration system and opposite to the first electret layer; and the first electret layer, the second electret layer and the third electret layer are parallel to one another.

Preferably, the vibration system comprises a diaphragm and a voice coil located below the diaphragm, and the first electret layer is attached to the diaphragm.

Preferably, the speaker device further comprises a first thermal resistance material layer arranged between the diaphragm and the voice coil and configured to isolate the first electret layer from the voice coil.

Preferably, the first thermal resistance material layer covers the whole area of the diaphragm, or is arranged only at an area where the diaphragm is connected to the voice coil.

Preferably, the diaphragm comprises a diaphragm body part and a reinforcing part; the diaphragm body part includes a plane part located in the middle and a surround part located at the edge of the plane part; the reinforcing part is arranged above the plane part; and the first electret layer is arranged at the side, close to the voice coil, of the plane part, or is arranged at the side, close to the reinforcing part, of the plane part, or is arranged above the reinforcing part.

Preferably, the speaker device further comprises the first thermal resistance material layer arranged between the diaphragm and the voice coil and configured to isolate the first electret layer from the voice coil.

Preferably, the first thermal resistance material layer covers the whole area of the diaphragm body part, or only covers the whole area of the plane part, or is arranged only at the area where the diaphragm is connected to the voice coil.

Preferably, each of the first electret layer, the second electret layer and the third electret layer is provided with the same number of independent areas. All of the independent areas have the same shape and size. All of the independent areas of the first electret layer are equal in electric charge quantity and are symmetrically distributed with respect to a center point of the diaphragm. All of the independent areas of the second electret layer are equal in electric charge quantity and are in one-to-one correspondence with the independent areas of the first electret layer. All of the independent areas of the third electret layer are equal in electric charge quantity and are in one-to-one correspondence with the independent areas of the first electret layer.

Preferably, the diaphragm comprises a diaphragm body part and a reinforcing part connected with the former; and all of the independent areas of the first electret layer are distributed at the edge of a connection area of the diaphragm body part and the reinforcing part.

Preferably, the shell comprises a front cover arranged above the vibration system; and the second electret layer is attached to the front cover and arranged at the side, facing the vibration system, of the front cover.

Preferably, the vibration system comprises the diaphragm and the voice coil located below the diaphragm; the magnetic circuit system is located below the vibration system, and comprises a washer; and the third electret layer is attached to the washer and arranged to the side, close to the diaphragm, of the washer.

Preferably, the speaker device further comprises a second thermal resistance material layer arranged between the third electret layer and the washer.

Preferably, the first electret layer, the second electret layer and the third electret layer are electret thin films or electret plates.

Preferably, the thicknesses of the first, second and third electret layers are in the scale of μm-mm.

Preferably, a material of the first electret layer, the second electret layer and the third electret layer comprises any one or a combination of a fluorinated ethylene propylene copolymer, polytetrafluoroethylene, polyvinylidene fluoride, polyethylene, polypropylene, polyetherimide, polyethylene terephthalate, expanded polytetrafluoroethylene, and polyvinylidene difluoride.

According to a second aspect of the present invention, there is provided a method for adjusting a diaphragm balance position of a speaker device. The method comprises the following steps: providing the speaker device as described above; and adjusting a ratio of an electric charge quantity $Q_2$ carried by a second electret layer to an electric charge quantity $Q_3$ carried by a third electret layer according to a formula $$\frac{Q_2}{Q_3} = \frac{d_1^2}{d_2^2},$$

so as to adjust the balance position of the diaphragm, wherein a distance between the first electret layer and the second electret layer is $d_1$, and a distance between the first electret layer and the third electret layer is $d_2$.

According to a third aspect of the present invention, there is provided a method for adjusting diaphragm compliance performance of a speaker device. The method comprises the following steps: providing the speaker device as described above; and adjusting an electric charge quantity $Q_1$ carried by a first electret layer, an electric charge quantity $Q_2$ carried by a second electret layer and an electric charge quantity $Q_3$ carried by a third electret layer, so as to adjust the compliance performance of the diaphragm.

The inventor of the present invention found that in the prior art, polarization of a speaker product only can be alleviated by a spider, but this method has its own limitation. In order to avoid the polarization phenomenon of the speaker product, the present invention provides a technical scheme for restraining the polarization of the speaker by use of an electrostatic field force. This direction of solving the problem is never considered or expected by a person skilled in the art. Thus, the present invention provides new technical solutions.

In the present invention, the electrostatic field force is adopted to restrain the polarization of the diaphragm in the vibration direction, and is provided by the electret layers, so that externally provided excitation signal is not required. Moreover, an assembling process is simple, and a restraining effect is good.

Further features of the present invention and advantages thereof will become apparent from the following detailed description of exemplary embodiments according to the present invention with reference to the attached drawings.

BRIEF DESCRIPTION OF THE DRAWINGS

The accompanying drawings, which are incorporated in and constitute a part of the specification, illustrate embodiments of the invention and, together with the description thereof, serve to explain the principles of the invention.

DETAILED DESCRIPTION

Figure 1:
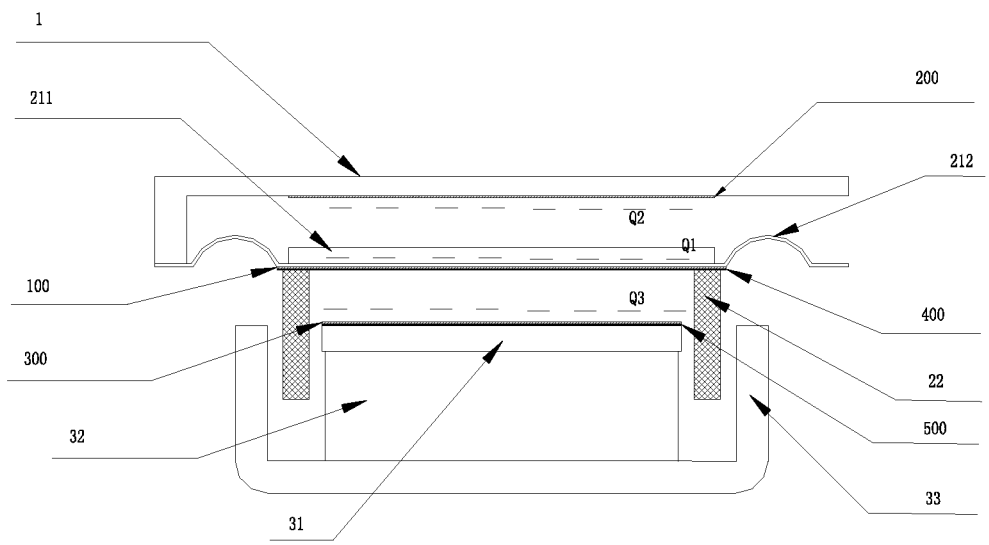
FIG. 1 is a schematically structural view of a speaker device capable of restraining polarization according to a first embodiment of the present invention.

Various exemplary embodiments of the present invention will now be described in detail with reference to the drawings. It should be noted that the relative arrangement of the components and steps, the numerical expressions, and numerical values set forth in these embodiments do not limit the scope of the present invention unless it is specifically stated otherwise.

The following description of at least one exemplary embodiment is merely illustrative in nature and is in no way intended to limit the invention, its application, or uses.

Techniques, methods and apparatus as known by one of ordinary skill in the relevant art may not be discussed in detail but are intended to be part of the specification where appropriate.

In all of the examples illustrated and discussed herein, any specific values should be interpreted to be illustrative only and non-limiting. Thus, other examples of the exemplary embodiments could have different values.

Notice that similar reference numerals and letters refer to similar items in the following figures, and thus once an item is defined in one figure, it is possible that it need not be further discussed in the accompanying drawings.

A speaker device capable of restraining polarization, provided by the present invention, comprises a vibration system, a magnetic circuit system, a shell accommodating the vibration system and the magnetic circuit system, a first electret layer, a second electret layer and a third electret layer, wherein the first electret layer, the second electret layer and the third electret layer have the same electric charge polarity; the first electret layer is attached to the vibration system; the second electret layer is attached to a first fixing component above the vibration system and opposite to the first electret layer; the third electret layer is attached to a second fixing component below the vibration system and opposite to the first electret layer; and the first electret layer, the second electret layer and the third electret layer are parallel to one another. In the present invention, electrostatic field force among the electret layers is adopted to restrain the polarization of the vibration system in a vibration direction, and the electrostatic field force is provided by repulsive forces among the electret layers. As an electret material can carry stable electric charges for a long time when being independent of an external power supply, the establishment of an electrostatic field is very simple.

The vibration system comprises a diaphragm and a voice coil located below the diaphragm, and the first electret layer is attached to the diaphragm. The speaker device further comprises a first thermal resistance material layer arranged between the diaphragm and the voice coil and configured to isolate the first electret layer from the voice coil. The first thermal resistance material layer may cover the whole area of the diaphragm, or is arranged only at an area where the diaphragm is connected to the voice coil.

FIG. 1 shows a speaker device capable of restraining polarization according to a first embodiment. The speaker comprises a vibration system, a magnetic circuit system, and a shell accommodating the vibration system and the magnetic circuit system. The vibration system of the speaker includes a diaphragm and a voice coil 22 located below the diaphragm. The diaphragm comprises a diaphragm body part 212 and a reinforcing part 211. The diaphragm body part 212 includes a plane part located in the middle, a surround part located at the edge of the plane part, and a fixing part located at the outermost and fixed to the shell. The reinforcing part 211 is arranged above the plane part. The magnetic circuit system of the speaker is located below the vibration system and comprises a washer 31, a magnet 32 and a frame 33 sequentially from top to bottom. The shell comprises a front cover 1 arranged above the diaphragm.

As shown in FIG. 1, the first electret layer 100 is attached to the diaphragm and is arranged at the side, close to the voice coil 22, of the plane part. The first fixing component adopts the front cover 1, and the second electret layer 200 is attached to the front cover 1 and is arranged at the side, facing the vibration system, of the front cover 1. The second fixing component adopts the washer 31, and the third electret layer 300 is attached to the washer 31 and is arranged at the side, close to the diaphragm, of the washer 31. The first electret layer 100, the second electret layer 200 and the third electret layer 300 are parallel to one another and are consistent in polarity of the carried electric charges. For example, the carried electric charges may be positive charges shown in FIG. 1, or may be negative charges. The speaker device further comprises a first thermal resistance material layer 400 and a second thermal resistance material layer 500. The first thermal resistance material layer 400 is arranged between the diaphragm and the voice coil 22 and configured to isolate the first electret layer 100 from the voice coil 22; and the second thermal resistance material layer 500 is arranged between the third electret layer 300 and the washer 31. In this embodiment, the first thermal resistance material layer 400 only covers the whole area of the plane part.

Figure 4:
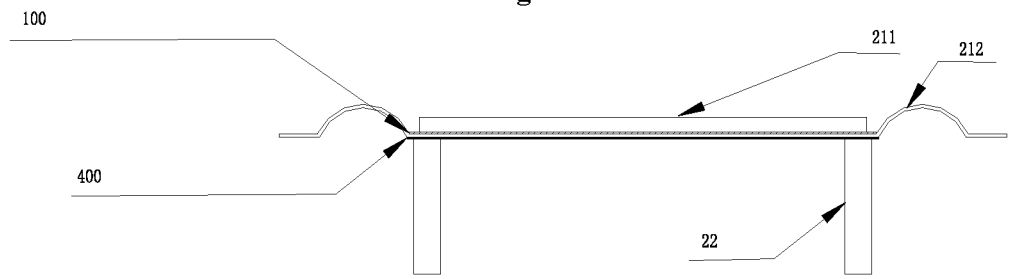
FIG. 4 is a schematically partial structure view of a speaker device capable of restraining polarization according to a second embodiment of the present invention.

FIG. 4 shows a speaker device capable of restraining polarization according to a second embodiment. The difference between the first embodiment and the second embodiment lies in that the first electret layer 100 is arranged at the side, close to the reinforcing part 211, of the plane part; and the first thermal resistance material layer 400 only covers the whole area of the plane part.

Figure 5:
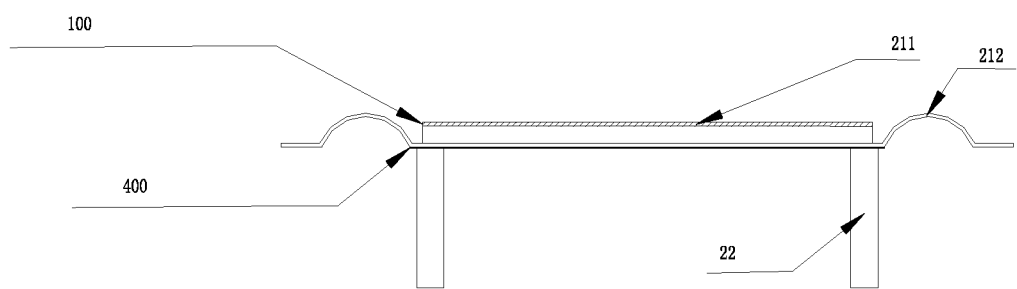
FIG. 5 is a schematically partial structure view of a speaker device capable of restraining polarization according to a third embodiment of the present invention.

FIG. 5 shows a speaker device capable of restraining polarization according to a third embodiment. The difference between the first embodiment and the third embodiment lies in that the first electret layer 100 is arranged above the reinforcing part 211; and the first thermal resistance material layer 400 only covers the whole area of the plane part.

Figure 6:
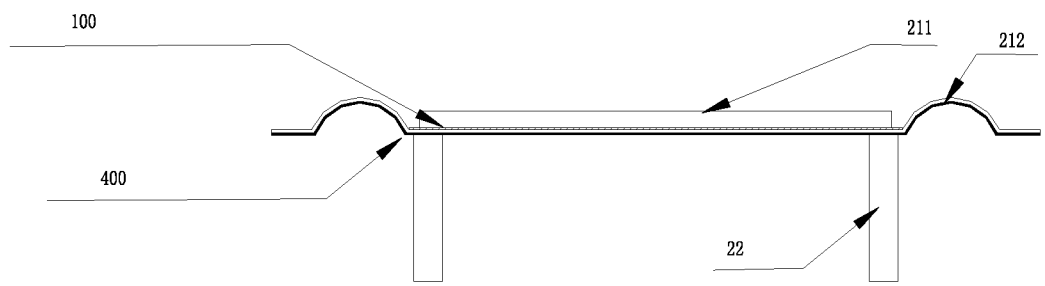
FIG. 6 is a schematically partial structure view of a speaker device capable of restraining polarization according to a fourth embodiment of the present invention.
Figure 7A:
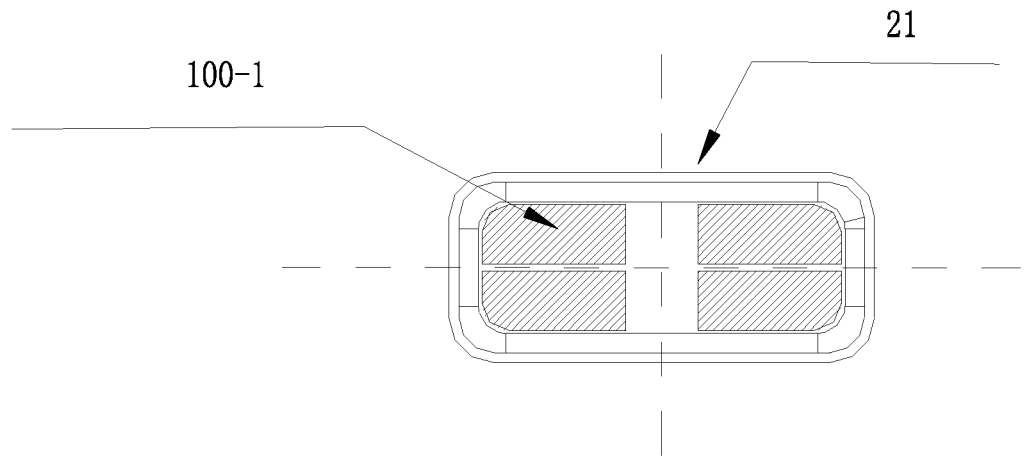
FIGS. 7a-7c are schematically structural views of a speaker device capable of restraining polarization according to a fifth embodiment of the present invention.
Figure 7B:
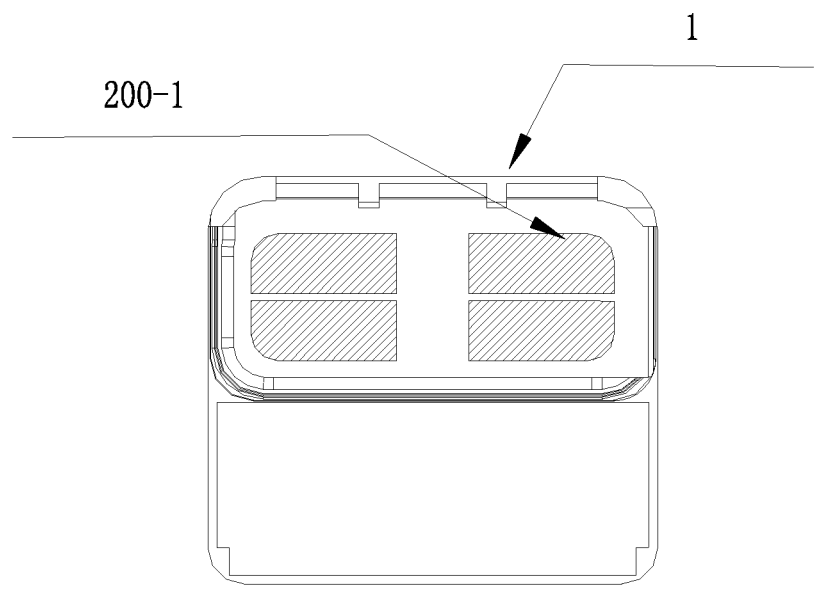
Figure 7C:
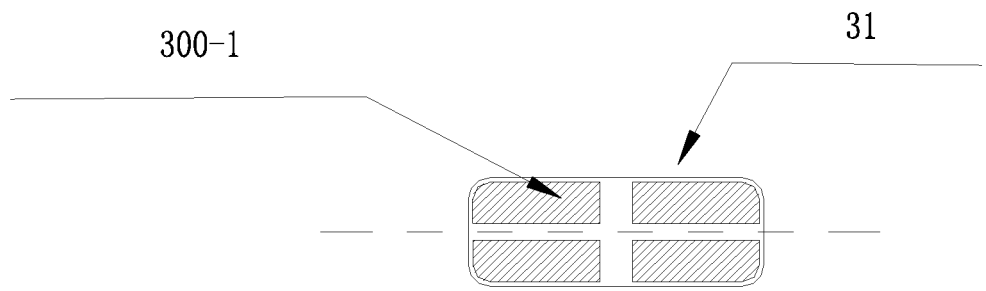
Figure 8:
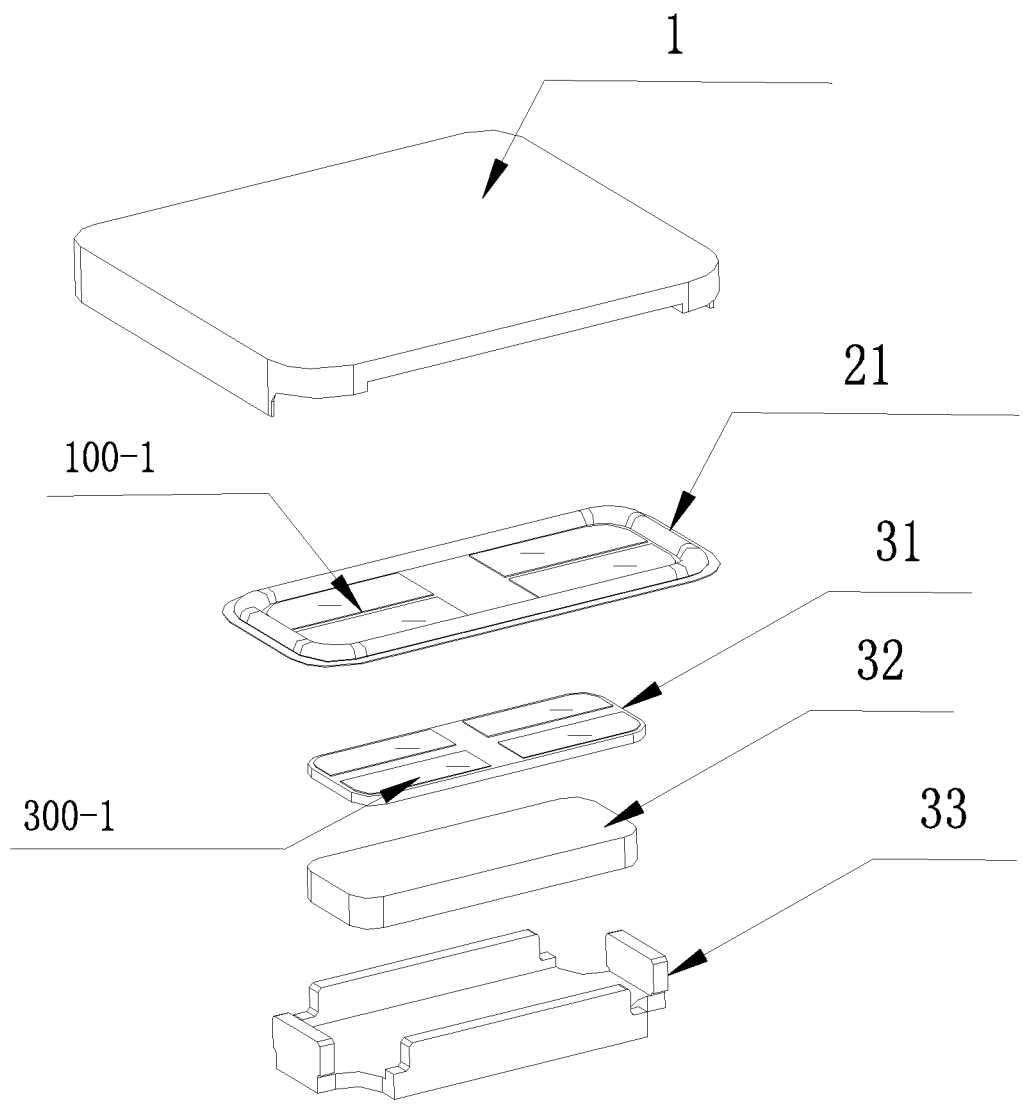
FIGS. 8-9 respectively show exploded views of the speaker device capable of restraining polarization according to the fifth embodiment of the present invention.
Figure 9:
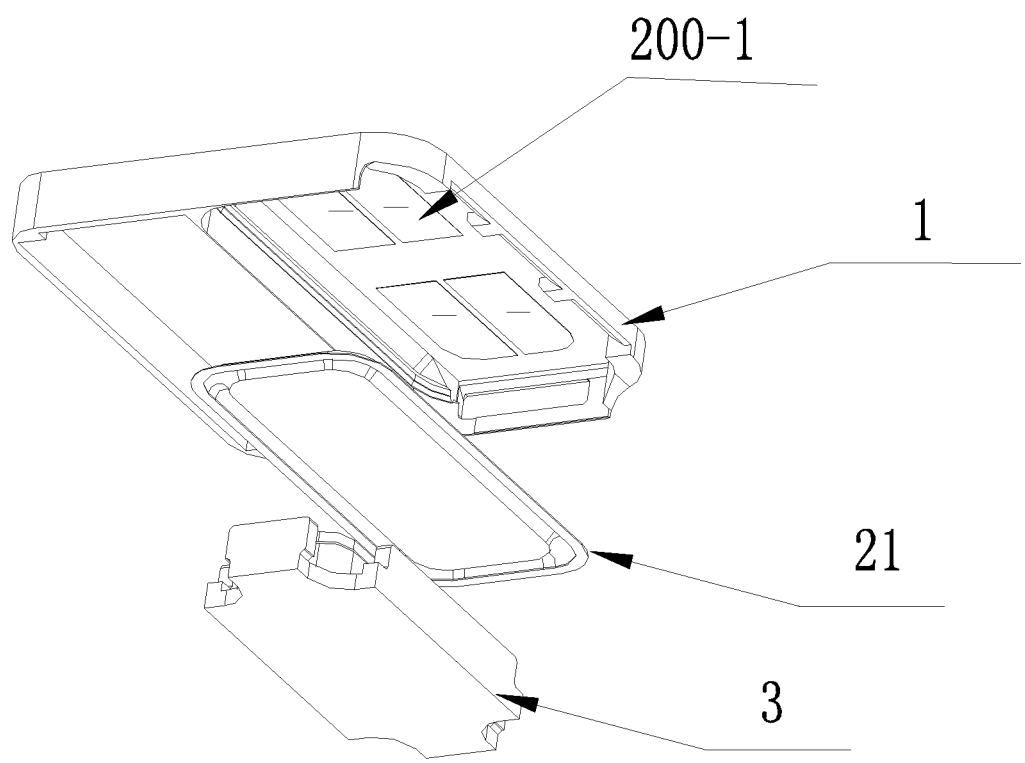

FIG. 6 shows a speaker device capable of restraining polarization according to a fourth embodiment. The difference between the first embodiment and the fourth embodiment lies in that the first electret layer 100 is arranged at the side, close to the reinforcing part 211, of the plane part; and the first thermal resistance material layer 400 covers the whole area of the diaphragm body part 212.

In general, the first electret layer 100 is arranged at the side, close to the voice coil 22, of the plane part, is arranged at the side, close to the reinforcing part 211, of the plane part, or is arranged above the reinforcing part 211. The first thermal resistance material layer is arranged between the diaphragm and the voice coil 22, is configured to isolate the first electret layer 100 from the voice coil 22, may cover the whole area of the diaphragm body part 212, or may only cover the whole area of the plane part, or is arranged only at an area where the diaphragm is connected to the voice coil 22. The second thermal resistance material layer 500 is arranged between the third electret layer 300 and the washer 31.

FIGS. 7a-7c and 8-9 respectively show a speaker device capable of restraining polarization according to a fifth embodiment. The speaker device comprises a front cover 1, a vibration system and a magnetic circuit system 3 sequentially from top to bottom. The vibration system includes a diaphragm 21 and a voice coil (not shown in the drawings). The magnetic circuit system comprises a washer 31, a magnet 32 and a frame 33 sequentially from top to bottom. The first electret layer is attached to the diaphragm 21, and is specifically arranged above the reinforcing part 211. The second electret layer is attached to the front cover 1 and is arranged at the side, facing the vibration system, of the front cover 1. The third electret layer is attached to the washer 31, and is arranged at the side, close to the diaphragm 21, of the washer 31. The fifth embodiment differs from the first embodiment in that each of the first electret layer, the second electret layer and the third electret layer includes four independent areas which are the same in shape and size. The four independent areas 100-1 of the first electret layer 100 are equal in electric charge quantity, are symmetrically distributed with respect to a center point of the diaphragm 21, and are close to the edge of a connection area of the diaphragm body part 212 and the reinforcing part 211. The four independent areas 200-1 of the second electret layer 200 are equal in electric charge quantity and are in one-to-one correspondence with the four independent areas 100-1 of the first electret layer 100. The four independent areas 300-1 of the third electret layer 300 are equal in electric charge quantity and are in one-to-one correspondence with the four independent areas 100-1 of the first electret layer 100. With this arrangement, displacements at four corners of the diaphragm 21 are restrained via the independent electrets respectively, so that the restraining effect is better.

The first electret layer 100, the second electret layer 200 and the third electret layer 300 may be electret thin films or electret plates. The thicknesses of the first, second and third electret layers are in the scale of μm-mm. The material of the first, second and third electret layers comprises any one or a combination of a fluorinated ethylene propylene copolymer, polytetrafluoroethylene, polyvinylidene fluoride, polyethylene, polypropylene, polyetherimide, polyethylene terephthalate, expanded polytetrafluoroethylene, and polyvinylidene difluoride.

Each of the electret layers may be attached by coating the electret material or bonding the electret thin film/electret plate.

Figure 2:
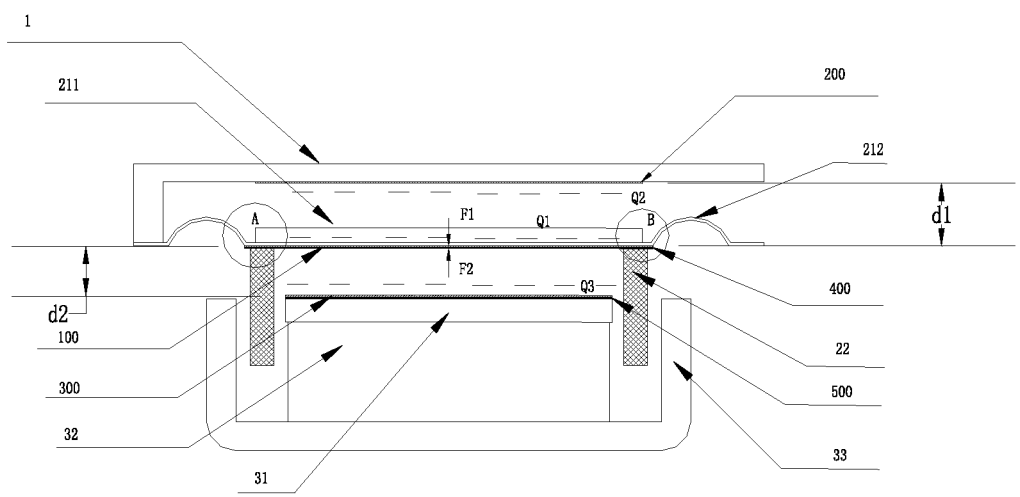
FIGS. 2-3 respectively show schematic views of the principle of the speaker device capable of restraining polarization of the present invention.

The principle of the speaker device capable of restraining polarization provided by the present invention is described with reference to FIGS. 2 and 3. In the present invention, the polarity of the electric charges carried by the first electrets layer 100, the second electret layer 200 and the third electret layer 300 is the same. The electric charge quantities carried by the first, second and third electret layers 100, 200 and 300 are $Q_1$, $Q_2$ and $Q_3$, respectively. A distance between the first electret layer 100 and the second electret layer 200 is $d_1$, and a distance between the first electret layer 100 and the third electret layer 300 is $d_2$. As shown in FIG. 2, the first electret layer 100 is subjected to a downward repulsive force F1 and an upward repulsive force F2, so F1=F2 should be satisfied when the diaphragm 21 is in a stationary state without working, and $$\frac{Q_2}{Q_3} = \frac{d_1^2}{d_2^2}$$

should be satisfied according to an electrostatic force formula.

Figure 3:
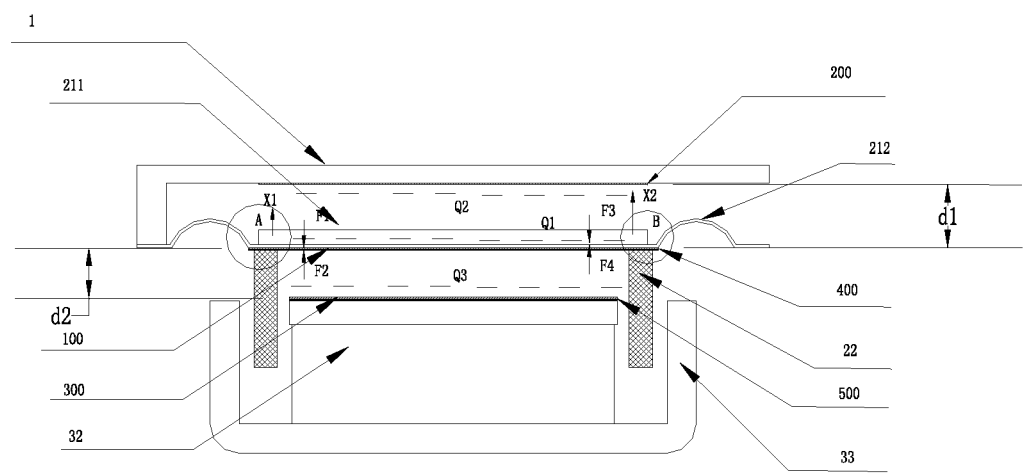

It can be seen from FIG. 3 that a point A is subjected to the downward repulsive force F1 and the upward repulsive force F2, so that a resultant force at the point A is equal to F1-F2. A point B is subjected to a downward repulsive force F3 and an upward repulsive force F4, so that a resultant force at the point B is equal to F3-F4. In the absence of polarization, F1 is equal to F3, and F2 is equal to F4. If displacements of the diaphragm 21 in the vibration direction are unbalanced, polarization will occur. For example, if an upward vibration displacement X2 at the point B is greater than an upward vibration displacement X1 at the point A, a distance from the point B to the front cover 1 is shorter than that from the point A to the front cover 1, resulting in F3>F1 and F4<F2. It shows that the force, opposite to the displacement, at the point B is greater than that at the point A. Thus, it can be seen that this polarization can be well restrained in the present invention.

It can be seen from the above that a ratio of the electric charge quantity $Q_2$ carried by the second electret layer 200 to the electric charge quantity $Q_3$ carried by the third electret layer 300 can be adjusted according to a formula $$\frac{Q_2}{Q_3} = \frac{d_1^2}{d_2^2},$$

so as to adjust the balance position of the diaphragm 21. The present invention further provides a method for adjusting a diaphragm balance position of a speaker device. The method comprises the following steps: providing the speaker device as described above; and adjusting the ratio of the electric charge quantity $Q_2$ carried by the second electret layer to the electric charge quantity $Q_3$ carried by the third electret layer according to the formula $$\frac{Q_2}{Q_3} = \frac{d_1^2}{d_2^2},$$

so as to adjust the balance position of the diaphragm, wherein the distance between the first electret layer and the second electret layer is $d_1$, and the distance between the first electret layer and the third electret layer is $d_2$. It should be noted that this adjustment step may be carried out after the manufacture of the speaker device is completed, or may be carried out in a speaker device manufacturing process.

In a vibration process, the voice coil 22 is not only affected by compliance performance of the diaphragm 21, but also subjected to electrostatic field actions from the electret layers above and below the diaphragm 21. The electrostatic field provides an electrostatic force similar to a restoring force to the diaphragm 21, such that this electrostatic field also has an equivalent "compliance property". Therefore, the compliance performance of the diaphragm 21 can be adjusted by adjusting the $Q_1$, $Q_2$ and $Q_3$. The present invention further provides a method for adjusting the diaphragm compliance performance of the speaker device. The method comprises the following steps: providing the speaker device as described above; and adjusting the electric charge quantity $Q_1$ carried by the first electret layer, the electric charge quantity $Q_2$ carried by the second electret layer and the electric charge quantity $Q_3$ carried by the third electret layer, so as to adjust the compliance performance of the diaphragm. It should be noted that this adjustment step may be carried out after the manufacture of the speaker device is completed, or may be carried out in the speaker device manufacturing process.

The present invention has the following benefits.

(1) The restoring force of the electrostatic field restrains the polarization of the diaphragm in a contactless manner, so that the assembling process is simple.

(2) The electret layers with the electric charges are independent of one another, so that an externally provided excitation signal is not required.

(3) A resting position of the diaphragm may be adjusted by adjusting the electric charge quantities $Q_2$ and $Q_3$, so that direct current offset of the speaker product under a low frequency is reduced, improving a harmonic distortion situation of the product.

(4) Non-linearity of the equivalent compliance performance of the electrostatic field in the present invention can be calculated, so that the compliance performance of the diaphragm and the whole vibration system can be adjusted by adjusting the electric charge quantities $Q_1$, $Q_2$ and $Q_3$.

Although some specific embodiments of the present invention have been demonstrated in detail with examples, it should be understood by a person skilled in the art that the above examples are only intended to be illustrative but not to limit the scope of the present invention. It should be understood by those skilled in the art that the above embodiments can be modified without departing from the scope and spirit of the present invention. The scope of the present invention is defined by the claims.

The invention claimed is:

1. A speaker device capable of restraining polarization, comprising:

a vibration system, a magnetic circuit system, a shell accommodating the vibration system and the magnetic circuit system, a first electret layer, a second electret layer and a third electret layer, wherein the first electret layer, the second electret layer and the third electret layer have the same electric charge polarity;

the first electret layer is attached to the vibration system; the second electret layer is attached to a first fixing component above the vibration system and opposite to the first electret layer; the third electret layer is attached to a second fixing component below the vibration system and opposite to the first electret layer; and the first electret layer, the second electret layer and the third electret layer are parallel to one another;

the vibration system comprises a diaphragm and a voice coil located below the diaphragm, and the first electret layer is attached to the diaphragm; and a first thermal resistance material layer is arranged between the diaphragm and the voice coil and configured to isolate the first electret layer from the voice coil.

2. The device of claim 1, wherein the first thermal resistance material layer covers the whole area of the diaphragm, or is arranged only at an area where the diaphragm is connected to the voice coil.

3. The device of claim 1, wherein the diaphragm comprises a diaphragm body part and a reinforcing part; the diaphragm body part includes a plane part located in the middle and a surround part located at the edge of the plane part; the reinforcing part is arranged above the plane part; and the first electret layer is arranged at the side, close to the voice coil, of the plane part, or is arranged at the side, close to the reinforcing part, of the plane part, or is arranged above the reinforcing part.

4. The device of claim 3, wherein the first thermal resistance material layer covers the whole area of the diaphragm body part, or only covers the whole area of the plane part, or is arranged only at the area where the diaphragm is connected to the voice coil.

5. The device of claim 1, wherein each of the first electret layer, the second electret layer and the third electret layer is provided with the same number of independent areas; all of the independent areas have the same shape and size; all of the independent areas of the first electret layer are equal in electric charge quantity and are symmetrically distributed with respect to a center point of the diaphragm; all of the independent areas of the second electret layer are equal in electric charge quantity and are in one-to-one correspondence with the independent areas of the first electret layer; and all of the independent areas of the third electret layer are equal in electric charge quantity and are in one-to-one correspondence with the independent areas of the first electret layer.

6. The device of claim 5, wherein the diaphragm comprises a diaphragm body part and a reinforcing part connected with the diaphragm body part; and all of the independent areas of the first electret layer are distributed at the edge of a connection area of the diaphragm body part and the reinforcing part.

7. The device of claim 1, wherein the shell comprises a front cover arranged above the vibration system; and the second electret layer is attached to the front cover and arranged at the side, facing the vibration system, of the front cover.

8. The device of claim 1, wherein the vibration system comprises a diaphragm and a voice coil located below the diaphragm; the magnetic circuit system is located below the vibration system, and comprises a washer; and the third electret layer is attached to the washer and arranged to the side, close to the diaphragm, of the washer.

9. The device of claim 8, further comprising a second thermal resistance material layer arranged between the third electret layer and the washer.

10. The device of claim 1, wherein the first electret layer, the second electret layer and the third electret layer are electret thin films or electret plates.

11. The device of claim 1, wherein the thicknesses of the first, second and third electret layers are in the scale of μm-mm.

12. The device of claim 1, wherein a material of the first electret layer, the second electret layer and the third electret layer comprises any one or a combination of a fluorinated ethylene propylene copolymer, polytetrafluoroethylene, polyvinylidene fluoride, polyethylene, polypropylene, polyetherimide, polyethylene terephthalate, expanded polytetrafluoroethylene, and polyvinylidene difluoride.

13. A method for adjusting a diaphragm balance position of a speaker device, the method comprising the following steps:
providing a speaker device capable of restraining polarization, comprising:
a vibration system, a magnetic circuit system, a shell accommodating the vibration system and the magnetic circuit system, a first electret layer, a second electret layer and a third electret layer, wherein the first electret layer, the second electret layer and the third electret layer have the same electric charge polarity;
the first electret layer is attached to the vibration system; the second electret layer is attached to a first fixing component above the vibration system and opposite to the first electret layer; the third electret layer is attached to a second fixing component below the vibration system and opposite to the first electret layer; and the first electret layer, the second electret layer and the third electret layer are parallel to one another; and
the vibration system comprises a diaphragm and a voice coil located below the diaphragm, and the first electret layer is attached to the diaphragm; and
adjusting a ratio of an electric charge quantity $Q_2$ carried by the second electret layer to an electric charge quantity $Q_3$ carried by the third electret layer according to a formula $$\frac{Q_2}{Q_3} = \frac{d_1^2}{d_2^2},$$

so as to adjust the balance position of the diaphragm, wherein a distance between the first electret layer and the second electret layer is $d_1$, and a distance between the first electret layer and the third electret layer is $d_2$.

14. A method for adjusting diaphragm compliance performance of a speaker device, the method comprising the following steps:
providing a speaker device capable of restraining polarization, comprising:
a vibration system, a magnetic circuit system, a shell accommodating the vibration system and the magnetic circuit system, a first electret layer, a second electret layer and a third electret layer, wherein the first electret layer, the second electret layer and the third electret layer have the same electric charge polarity;
the first electret layer is attached to the vibration system; the second electret layer is attached to a first fixing component above the vibration system and opposite to the first electret layer; the third electret layer is attached to a second fixing component below the vibration system and opposite to the first electret layer; and the first electret layer, the second electret layer and the third electret layer are parallel to one another; and
the vibration system comprises a diaphragm and a voice coil located below the diaphragm, and the first electret layer is attached to the diaphragm; and
adjusting an electric charge quantity $Q_1$ carried by the first electret layer, an electric charge quantity $Q_2$ carried by the second electret layer and an electric charge quantity $Q_3$ carried by the third electret layer, so as to adjust the compliance performance of the diaphragm.

* * * * *